United States Patent
Liu et al.

(10) Patent No.: US 9,919,073 B2
(45) Date of Patent: Mar. 20, 2018

(54) HYDROPHOBIC ADHESIVE WITH ABSORBENT FIBERS

(75) Inventors: Junkang J. Liu, Woodbury, MN (US); Cary A. Kipke, Woodbury, MN (US); Ting Fan, Shanghai (CN)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 793 days.

(21) Appl. No.: 14/237,367

(22) PCT Filed: Aug. 17, 2012

(86) PCT No.: PCT/US2012/051244
§ 371 (c)(1),
(2), (4) Date: Apr. 22, 2014

(87) PCT Pub. No.: WO2013/025955
PCT Pub. Date: Feb. 21, 2013

(65) Prior Publication Data
US 2014/0220843 A1    Aug. 7, 2014

Related U.S. Application Data

(60) Provisional application No. 61/524,545, filed on Aug. 17, 2011.

(51) Int. Cl.
*A61L 15/58* (2006.01)
*C09J 183/04* (2006.01)
(Continued)

(52) U.S. Cl.
CPC ......... *A61L 15/585* (2013.01); *A61L 24/0094* (2013.01); *A61L 28/0069* (2013.01);
(Continued)

(58) Field of Classification Search
CPC ...... C08J 83/04; C08G 77/455; A61L 15/585; A61L 24/0094; A61L 28/0069;
(Continued)

(56) References Cited

U.S. PATENT DOCUMENTS

| 4,157,418 A | 6/1979 | Heilmann |
| 4,366,814 A * | 1/1983 | Riedel ..................... A61L 15/24 428/197 |

(Continued)

FOREIGN PATENT DOCUMENTS

| DE | 102005005149 | 8/2006 |
| DE | 102009036612 | 2/2011 |

(Continued)

OTHER PUBLICATIONS

International Search Report for PCT International Application No. PCT/US2012/051244 dated Nov. 5, 2012, 5 pages.

*Primary Examiner* — Arti Singh-Pandey
(74) *Attorney, Agent, or Firm* — 3M Innovative Properties Company; Lynn R. Hunsberger

(57) ABSTRACT

The disclosed hydrophobic adhesive composition comprises a hydrophobic adhesive matrix and water absorbent fibers dispersed throughout the adhesive matrix to provide water management capabilities to the adhesive composition. The disclosed adhesive composition can adhered to a variety of surfaces, such as skin, and will easily remove from the surface. Therefore, the disclosed adhesive is particularly well suitable for application to skin wherein the absorbent fiber can absorb perspiration, water, or wound fluid from skin.

14 Claims, 1 Drawing Sheet

(51) Int. Cl.
*C09J 183/10* (2006.01)
*A61L 24/00* (2006.01)
*A61L 28/00* (2006.01)
*C08G 77/455* (2006.01)
*C08K 7/02* (2006.01)

(52) U.S. Cl.
CPC ............ *C09J 183/04* (2013.01); *C09J 183/10* (2013.01); *A61L 2400/14* (2013.01); *A61L 2420/04* (2013.01); *C08G 77/455* (2013.01); *C08K 7/02* (2013.01); *Y10T 428/249983* (2015.04); *Y10T 428/269* (2015.01); *Y10T 428/2809* (2015.01); *Y10T 442/2738* (2015.04)

(58) Field of Classification Search
CPC ... A61L 2400/14; A61L 2420/04; C08K 7/02; C09J 183/04; C09J 183/10; Y10T 428/249983; Y10T 428/428269; Y10T 428/2809; Y10T 442/2738
USPC ...... 428/317.3, 339, 345; 442/149; 524/504, 524/506
See application file for complete search history.

(56) References Cited

U.S. PATENT DOCUMENTS

| | | | |
|---|---|---|---|
| 4,538,603 A | 9/1985 | Pawelchak | |
| 5,432,000 A * | 7/1995 | Young, Sr. | D04H 1/425 428/357 |
| 5,540,922 A | 7/1996 | Fabo | |
| 5,681,579 A | 10/1997 | Freeman | |
| 6,075,177 A | 6/2000 | Bahia | |
| 6,095,996 A * | 8/2000 | Steer | A61L 15/585 428/355 AC |
| 6,803,420 B2 | 10/2004 | Cleary | |
| 7,842,752 B2 | 11/2010 | Bougherara | |
| 7,858,157 B2 | 12/2010 | Busam | |
| 2004/0082925 A1* | 4/2004 | Patel | A61L 15/44 604/289 |
| 2004/0175344 A1 | 9/2004 | Woller | |
| 2007/0060855 A1 | 3/2007 | Leung | |
| 2008/0318057 A1 | 12/2008 | Sherman | |
| 2009/0076186 A1 | 3/2009 | Lassalle | |
| 2011/0100528 A1 | 5/2011 | Ronner | |
| 2013/0040126 A1* | 2/2013 | Pett | C09D 1/00 428/312.6 |

FOREIGN PATENT DOCUMENTS

| | | |
|---|---|---|
| EP | 0822950 | 2/1998 |
| EP | 0880973 | 12/1998 |
| JP | 1992-303445 | 10/1992 |
| WO | WO 2005-021058 | 3/2005 |
| WO | WO 2006-111654 | 10/2006 |
| WO | WO 2010-056544 | 5/2010 |
| WO | WO 2011-005846 | 1/2011 |
| WO | WO 2013-025579 | 2/2013 |

* cited by examiner

# HYDROPHOBIC ADHESIVE WITH ABSORBENT FIBERS

This application is a national stage filing under 35 U.S.C. 371 of PCT/US2012/051244, filed Aug. 17, 2012, which claims priority to U.S. Provisional Application No. 61/524,545, filed Aug. 17, 2011, the disclosures of which are incorporated by reference in their entirety herein.

BACKGROUND

The present disclosure relates to a hydrophobic adhesive with absorption capabilities. In particular, the present disclosure relates to a hydrophobic adhesive comprising a water absorbent fiber dispersed in the adhesive.

Silicone adhesives are useful for medical tapes and dressings because the silicone adhesive can provide adhesion while gently removing from the skin without causing trauma or stripping skin cells or hair. The skin and especially a wound may produce moisture. Silicone adhesives are generally very hydrophobic and do not allow for fluid absorption or fluid passage. Therefore, moisture from the skin can weaken the adhesive bonding to skin and cause the adhesive to lift from the skin.

Complicated tape and dressing designs have been created to allow for fluid passage. For example, U.S. Pat. No. 5,540,922, discloses a silicone adhesive on a supporting film, wherein the silicone adhesive and supporting film are perforated to allow for fluid passage. However, a perforated silicone and film system is not ideal for all applications because incomplete surface coverage of the adhesive from perforations reduces the adhesion and securement ability of the adhesive.

Other designs have been created that manipulate the adhesive composition. For example, a hydrophilic silicone could be blended with a hydrophobic silicone to improve moisture absorption, see for example U.S. Pat. No. 7,842,752. In other designs, incorporation of absorbent particles into a hydrophobic adhesive can help with increasing absorbency. However, for either the ability of the adhesive system to absorb water is limited.

SUMMARY

The disclosed hydrophobic adhesive composition comprises a hydrophobic adhesive matrix and water absorbent fibers dispersed throughout the adhesive matrix to provide water management capabilities to the adhesive composition. The disclosed adhesive composition can adhere to a variety of surfaces, such as skin, and will easily remove from the surface. Therefore, the disclosed adhesive is particularly well suited for application to skin wherein the absorbent fiber can absorb perspiration, water, or wound fluid from skin.

In one embodiment, the adhesive composition comprises a radiation crosslinked hydrophobic adhesive and a plurality of water absorbent fibers dispersed throughout the hydrophobic adhesive. At least a portion of the fibers are exposed at an outer surface of the adhesive composition and at least a portion of the fibers contact one another at mutual points of contact.

In another embodiment, the adhesive composition comprises an adhesive matrix consisting of a hydrophobic adhesive and a plurality of water absorbent fibers dispersed throughout the adhesive matrix. At least a portion of the fibers are exposed at an outer surface of the adhesive composition and at least a portion of the fibers contact one another at mutual points of contact.

In one embodiment, the hydrophobic adhesive is a hydrophobic silicone. In one embodiment, the silicone comprises a crosslinked poly diorganosiloxane. In one embodiment, the poly diorganosiloxane material comprises a poly dimethylsiloxane. In one embodiment, the poly dimethylsiloxane is selected from the group consisting of one or more silanol terminated poly dimethylsiloxanes, one or more non-functional poly dimethylsiloxanes, and combinations thereof. In one embodiment, the poly dimethylsiloxane consists of one or more non-functional poly dimethylsiloxanes. In one embodiment, the adhesive further comprises a silicate resin tackifier. In one embodiment, the adhesive further comprises a poly(dimethylsiloxane-oxamide) linear copolymer.

In one embodiment, the absorbent fiber comprises a natural hydrophilic fiber, synthetic hydrophilic fiber, semi-synthetic hydrophilic fiber, grafted hydrophilic fiber, a superabsorbent fiber or combinations thereof. In one embodiment, less than 30% wt. of the adhesive composition is the absorbent fiber. In one embodiment, between 0.1% and 10% wt. of the adhesive composition is the absorbent fiber.

In one embodiment, a medical article comprises a layer of the adhesive adhered to a medical substrate. In one embodiment, the layer of the adhesive has a thickness of 20 to 200 microns. In one embodiment, the medical substrate comprises at least one of paper, polymeric film, foam, woven fabric, foil, adhesive, gel, and non-woven fabric, or combinations of one or more thereof. In one embodiment, at least a portion of the water absorbent fibers contact the substrate.

In one embodiment, the hydrophobic adhesive is selected from the group consisting of a hydrophobic silicone, non polar acrylic, hydrophobic urethane, polyolefin, natural rubber, synthetic rubber, or combination of one or more thereof.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention.

The figures may not be drawn to scale.

DETAILED DESCRIPTION

Figure 1:
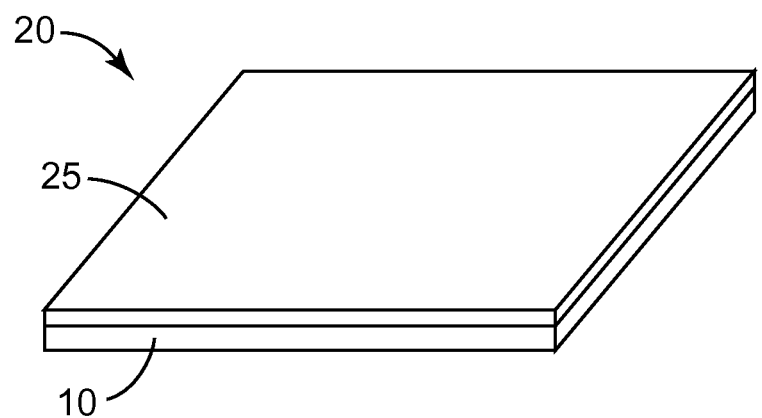
FIG. 1 is perspective view of an embodiment of an article with an adhesive composition applied to a substrate.
Figure 2:
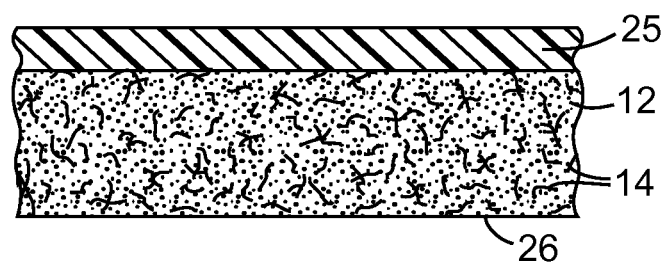
FIG. 2 is an enlarged side view of the article of FIG. 1.

FIG. 1 is a perspective view of an embodiment of an article 20 with an adhesive composition 10 applied to a substrate 25. FIG. 2 is an enlarged side view of the adhesive composition 10 applied to the substrate 25. The adhesive composition 10 comprises a plurality of water absorbent fibers 14 dispersed throughout an adhesive matrix 12 exposing a portion of the water absorbent fibers 14 at a skin-facing surface 26. The disclosed adhesive is particularly suitable for application to skin. Therefore, the article 20 can be a medical tape, bandage, or wound dressing utilizing various types of materials, e.g., film, fabric, paper, nonwoven, foam, adhesive, or combinations of one or more thereof.

The adhesive composition 10 comprises an adhesive matrix 12 and a water absorbent fiber 14 dispersed throughout the adhesive matrix. The adhesive matrix 12 is a hydrophobic adhesive. For application to skin, hydrophobic adhesives can provide adhesion but are much less likely to cause skin maceration that a hydrophilic adhesive. The adhesive matrix 12 could be any hydrophobic adhesive that can provide adhesion to a variety of surface, such as skin, while allowing for removal of the adhesive without damaging the surface. For example, the adhesive matrix may be a hydrophobic silicone adhesive, non-polar acrylic adhesive, hydrophobic urethane adhesive, polyolefin adhesive, natural rubber adhesive, and hydrophobic synthetic rubber adhesive, or combinations of one or more thereof. For any of these hydrophobic adhesives, if necessary, crosslinking can be achieved through a variety of known crosslinking techniques such as, for example, use of moisture, heat, or radiation in the presence or absence of a catalyst.

Manipulation of the absorbency properties of the adhesive composition through inclusion of a hydrophilic adhesive portion is not particularly effective at increasing absorption and can negatively impacts the adhesive properties of the hydrophobic adhesive. If the hydrophilic portion is completely blended with the hydrophobic portion, the adhesive properties of the hydrophobic adhesive are negatively impacted. If the blended adhesives form two phases, then the hydrophilic portion becomes trapped within the matrix of the hydrophobic portion and is therefore less effective at absorbing water. Further, inclusion of a hydrophilic adhesive can increase the possibility of skin maceration. Therefore, in one embodiment, the adhesive composition comprises an adhesive matrix consisting of a hydrophobic adhesive, such that the adhesive composition is essentially free of a hydrophilic adhesive segment.

For a medical article that will adhere to skin, it is desirable to be able to control the adhesive properties through either inclusion of a tackifier or control of crosslinking density (the chain length of the polymer between the crosslinks). Manipulating the chain length between crosslinks through a catalyzed thermal-cured adhesives is very challenging. Further, catalyzed thermal-curing systems are generally slow to make and therefore expensive. Therefore, it would be desirable to utilize a hydrophobic adhesive that does not cure through a catalyzed thermal-curing technique.

In one embodiment, radiation curing is particularly preferred technique because radiation process requires less space and less capital equipment as compared to catalyzed thermal curing. Also, radiation curing is relatively fast compared to thermal curing and is therefore significantly less expensive to make. Therefore, in one embodiment, the adhesive composition comprises a radiation crosslinked hydrophobic adhesive, such as disclosed in PCT Publication WO2010/056544, the disclosure of which is herein incorporated by reference.

In particular, radiation curing is accomplished through high energy radiation, such as electron beam or gamma ray radiation of hydrophobic adhesives, particularly without crosslinkable functional groups, such as defined in PCT Publication WO2010/056544, such as silicones. Silicones are particularly well suited for medical applications because of the inertness and biocompatibility of the material. Lightly crosslinked silicone gel adhesives are soft, tacky, elastic materials that have moderate adhesive strength compared to traditional, highly tackified silicone PSAs. These gel adhesives have excellent wetting characteristics due to their inherent low glass transition temperature, low surface energy, and relatively low storage modulus. The inertness and lack of reactivity of the silicone materials make silicone gels suitable for gentle-to-skin adhesive applications. Additionally, the elastic nature of the crosslinked gel and lack of interaction with hair surfaces debond the adhesives from skin by stretch releasing and further reduces the instances of pain during removal.

Generally, the silicone materials may be oils, fluids, gums, elastomers, or resins, e.g., friable solid resins. Generally, lower molecular weight, lower viscosity materials are referred to as fluids or oils, while higher molecular weight, higher viscosity materials are referred to as gums; however, there is no sharp distinction between these terms. Elastomers have even higher molecular weights than gums and typically do not flow at room temperature. As used herein, the terms "fluid" and "oil" refer to materials having a dynamic viscosity at 25° C. of no greater than 1,000,000 mPa·sec (e.g., less than 600,000 mPa·sec), while materials having a dynamic viscosity at 25° C. of greater than 1,000,000 mPa·sec (e.g., at least 10,000,000 mPa·sec) are referred to as "gums".

Generally, the silicone materials useful in the present disclosure are poly diorganosiloxanes, i.e., materials comprising a polysiloxane backbone. In some embodiments, the nonfunctionalized silicone materials can be described by the following formula illustrating a siloxane backbone with aliphatic and/or aromatic substituents:

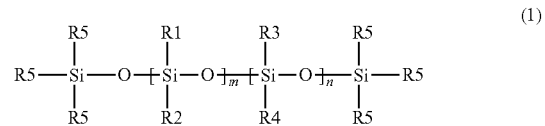

wherein R1, R2, R3, and R4 are independently selected from the group consisting of an alkyl group and an aryl group, each R5 is an alkyl group and n and m are integers, and at least one of m or n is not zero. In some embodiments, one or more of the alkyl or aryl groups may contain a halogen substituent, e.g., fluorine. For example, in some embodiments, one or more of the alkyl groups may be —CH$_2$CH$_2$C$_4$F$_9$.

In some embodiments, R5 is a methyl group, i.e., the nonfunctionalized poly diorganosiloxane material is terminated by trimethylsiloxy groups. In some embodiments, R1 and R2 are alkyl groups and n is zero, i.e., the material is a poly(dialkylsiloxane). In some embodiments, the alkyl group is a methyl group, i.e., poly(dimethylsiloxane) ("PDMS"). In some embodiments, R1 is an alkyl group, R2 is an aryl group, and n is zero, i.e., the material is a poly(alkylarylsiloxane). In some embodiments, R1 is methyl group and R2 is a phenyl group, i.e., the material is poly (methylphenylsiloxane). In some embodiments, R1 and R2 are alkyl groups and R3 and R4 are aryl groups, i.e., the material is a poly(dialkyldiarylsiloxane). In some embodiments, R1 and R2 are methyl groups, and R3 and R4 are phenyl groups, i.e., the material is poly(dimethyldiphenylsiloxane).

In some embodiments, the nonfunctionalized poly diorganosiloxane materials may be branched. For example, one or more of the R1, R2, R3, and/or R4 groups may be a linear or branched siloxane with alkyl or aryl (including halogenated alkyl or aryl) substituents and terminal R5 groups.

As used herein, "nonfunctional groups" are either alkyl or aryl groups consisting of carbon, hydrogen, and in some embodiments, halogen (e.g., fluorine) atoms. As used herein, a "nonfunctionalized poly diorganosiloxane material" is one in which the R1, R2, R3, R4, and R5 groups are nonfunctional groups.

Generally, functional silicone systems include specific reactive groups attached to the polysiloxane backbone of the starting material (for example, hydrogen, hydroxyl, vinyl, allyl, or acrylic groups). As used herein, a "functionalized poly diorganosiloxane material" is one in which at least one of the R-groups of Formula 2 is a functional group.

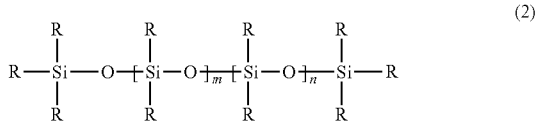

(2)

In some embodiments, a functional poly diorganosiloxane material is one is which at least 2 of the R-groups are functional groups. Generally, the R-groups of Formula 2 may be independently selected. In some embodiments, at least one functional group is selected from the group consisting of a hydride group, a hydroxy group, an alkoxy group, a vinyl group, an epoxy group, and an acrylate group.

In addition to functional R-groups, the R-groups may be nonfunctional groups, e.g., alkyl or aryl groups, including halogenated (e.g., fluorinated) alky and aryl groups. In some embodiments, the functionalized poly diorganosiloxane materials may be branched. For example, one or more of the R groups may be a linear or branched siloxane with functional and/or non-functional substituents.

The gentle to skin adhesives of the present disclosure may be prepared by combining one or more poly diorganosiloxane materials (e.g., silicone oils or fluids), optionally with an appropriate tackifying resin, coating the resulting combination, and curing using electron beam (E-beam) or gamma irradiation. Generally, any known additives useful in the formulation of adhesives may also be included.

If included, generally, any known tackifying resin may be used, e.g., in some embodiments, silicate tackifying resins may be used. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000-gm/mole, e.g., 500 to 15,000 gm/mole and generally W groups are methyl groups.

MQ silicate tackifying resins are copolymeric resins where each M unit is bonded to a Q unit, and each Q unit is bonded to at least one other Q unit. Some of the Q units are bonded to only other Q units. However, some Q units are bonded to hydroxyl radicals resulting in $HOSiO_{3/2}$ units (i.e., "$T^{OH}$" units), thereby accounting for some silicon-bonded hydroxyl content of the silicate tackifying resin.

The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having M, Q and D units. In some embodiments, some of the methyl R' groups of the D units can be replaced with vinyl (CH2=CH—) groups ("$D^{Vi}$" units). MQT silicate tackifying resins are terpolymers having M, Q and T units.

Suitable silicate tackifying resins are commercially available from sources such as Dow Corning (e.g., DC2-7066), Momentive Performance Materials (e.g., SR545 and SR1000), and Wacker Chemie AG (e.g., BELSIL TMS-803).

The polysiloxane material, the tackifying resin, if present, and any optional additives may be combined by any of a wide variety of known means prior to being coated and cured. For example, in some embodiments, the various components may be pre-blended using common equipment such as mixers, blenders, mills, extruders, and the like.

In some embodiments, the materials may be dissolved in a solvent, coated, and dried prior to curing. In some embodiments, solventless compounding and coating processes may be used. In some embodiments, solventless coating may occur at about room temperature. For example, in some embodiments, the materials may have kinematic viscosity of no greater than 100,000 centistokes (cSt), e.g., no greater than 50,000 cSt. However, in some embodiments, hot melt coating processes such as extrusion may be used, e.g., to reduce the viscosity of higher molecular weight materials to values more suitable for coating. The various components may be added together, in various combinations or individually, through one or more separate ports of an extruder, blended (e.g., melt mixed) within the extruder, and extruded to form the hot melt coated composition.

Regardless of how it is formed, the coated compositions are radiation cured. In some embodiments, coating may be cured through exposure to E-beam irradiation. In some embodiments, the coating may be cured through exposure to gamma irradiation. In some embodiments, a combination of electron beam curing and gamma ray curing may be used. For example, in some embodiments, the coating may be partially cured by exposure to electron beam irradiation. Subsequently, the coating may be further cured by gamma irradiation.

A variety of procedures for E-beam and gamma ray curing are well-known. The cure depends on the specific equipment used, and those skilled in the art can define a dose calibration model for the specific equipment, geometry, and line speed, as well as other well understood process parameters.

Commercially available electron beam generating equipment is readily available. For the examples described herein, the radiation processing was performed on a Model CB-300 electron beam generating apparatus (available from Energy Sciences, Inc. (Wilmington, Mass.). Generally, a support film (e.g., polyester terephthalate support film) runs through a chamber. In some embodiments, a sample of uncured material with a liner (e.g., a fluorosilicone release liner) on both sides ("closed face") may be attached to the support film and conveyed at a fixed speed of about 6.1 meters/min (20 feet/min) In some embodiments, a sample of the uncured material may be applied to one liner, with no liner on the opposite surface ("open face"). Generally, the chamber is inerted (e.g., the oxygen-containing room air is replaced with an inert gas, e.g., nitrogen) while the samples are e-beam cured, particularly when open-face curing.

The uncured material may be exposed to E-beam irradiation from one side through the release liner. For making a single layer laminating adhesive type tape, a single pass through the electron beam may be sufficient. Thicker samples, may exhibit a cure gradient through the cross section of the adhesive so that it may be desirable to expose the uncured material to electron beam radiation from both sides.

Commercially available gamma irradiation equipment includes equipment often used for gamma irradiation sterilization of products for medical applications. In some embodiments, such equipment may be used to cure, or partially cure the gentle to skin adhesives of the present disclosure. In some embodiments, such curing may occur simultaneously with a sterilization process for a semi-finished or finished product, for example a tape or wound dressing.

The adhesive composition 10 includes a plurality of water absorbent fibers 14 dispersed throughout the hydrophobic adhesive matrix 12. To aid in absorbency, at least a portion of the fibers are exposed at an outer surface of the adhesive composition. Further, at least a portion of the water absorbent fibers 14 contact one another at mutual points of contact or one fiber may also contact itself throughout the adhesive matrix 12.

The water absorbent fibers 14 can be any hydrophilic or hydrophilic modified fiber that is capable of absorbing water. The water absorbent fiber 14 removes moisture at the outer surface of the adhesive composition and carries the moisture into the network of water absorbent fibers 14. For example, when the adhesive composition 10 is applied to skin, the article 20 has a skin-facing surface 26 with a portion of exposed water absorbent fibers 14 that absorb moisture from the skin or wound. By managing the fluid at the skin contact surface 26, the adhesive composition 10 is able to maintain securement to the skin or wound for a longer period of time.

It has been found that water absorbent fibers are extremely useful in absorbing moisture as compared to water absorbent particles. It is believe that water absorbent particles become trapped within the hydrophobic adhesive and therefore have very limited water absorbent capabilities because the fluid is unable to penetrate to the trapped particles rendering them useless. To overcome this problem, the loading of water absorbent particles must be relatively high. This high loading of water absorbent particles negatively impacts the adhesive properties of the hydrophobic adhesive.

Water absorbing fibers 14 provide a fluid conduit from the skin-contacting surface 26 of the adhesive composition 10 into the matrix of the adhesive. The water absorbent fibers 14 will typically contact one another, and may become somewhat entangled and interconnected, further enhancing the fluid path away from the skin-contacting surface 26 and into the adhesive matrix. In some embodiments, at least a portion of the water absorbent fibers 14 will contact the substrate 25 and therefore provide an outlet for the absorbed fluid to exit the article 10. The water absorbent fibers 14 increase the absorbency of the adhesive and in some embodiments increasing the MVTR of the adhesive composition 10 or coated article 20.

The water absorbent fibers 14 can be a natural hydrophilic fiber, synthetic hydrophilic fiber, functionalized hydrophilic fiber, combinations thereof. Examples of a natural hydrophilic fibers include cellulose-containing fibers, cotton, wool, linen, cocoa fibers. Examples of synthetic hydrophilic fibers include nylon, carboxy methyl cellulose (CMC), or crosslinked polyoxyethelenes, polyoxpropylenes, polyoxy (ethylene-propylene), crosslinked polyacrylate acids, poly acrylate acids, alginates, chitosan, regenerated cellulose, polysaccharides, and derivatives or mixtures thereof.

Functionalized hydrophilic fibers can be natural or synthetic fibers with hydrophilic functional groups attached thereto. The hydrophilic functional groups may be attached to the polymer through a variety of techniques. Radiation grafting of monomers, polymers, or copolymers to a fiber surface can be conducted using high energy radiation (e.g. gamma or electron beam). Irradiation of fibers in the presence of UV light and a photoinitiator has also been disclosed as a process for treating fibers to render the fibers more hydrophilic (U.S. Pat. No. 7,858,157B2). Alternatively, the chemical structure of a fiber can be modified by traditional chemical reactions in a suitable solvent. For example, U.S. Pat. No. 6,075,177 discloses the modification of cellulose filaments with a strong alkali and monochloroacetic acid.

Examples of hydrophilic functional groups include anionic groups (e.g. carboxylic acids, sulfonic acids) and their salts (e.g., sodium, potassium, and the like), cationic groups (e.g., quaternary ammonium salts), or non-charged, neutral functionalities such as glycols or acrylates, or combinations of one or more thereof.

For example, U.S. Patent Application 61/524,417, titled "Monomer-Grafted Fibers and Uses Thereof" filed on Aug. 17, 2011, the disclosure of which is herein incorporated by reference, discloses suitable grafted hydrophilic fibers and methods of making that could be utilized for the water absorbent fibers 14 herein. As disclosed therein, using high energy irradiation (e.g., e-beam irradiation, gamma irradiation) to initiate a grafting reaction, the need for various commonly used initiator reagents can be obviated, and the resulting grafted fiber (and ultimately, the wound dressing) is free of those initiator reagents used in, for example, grafting reactions initiated with ultraviolet light or thermal processes. Further, a plurality of fibers can be irradiated with high energy irradiation and reacted with hydrophilic monomers, and residual hydrophilic monomers, if present, can be removed with a washing process, providing a plurality of irradiated fibers having grafted pendant hydrophilic groups and a high level of purity, which is generally desirable in the production of wound dressing articles.

In one embodiment, the negatively charged anionic monomer has at least one ethylenically unsaturated group capable of undergoing free radical polymerization, and an additional anionic functional group. In some embodiments, the ethylenically unsaturated group is a (meth)acryloyl group or a vinyl group. The anionic monomer can be a weak acid, a strong acid, a salt of a weak acid, a salt of a strong acid, or combinations thereof. If the anionic monomer used to prepare a hydrophilic fiber includes a salt of a weak acid or a salt of a strong acid, the counter ions of these salts can be, but are not limited to, alkali metals, alkaline earth metals, ammonium ions, or tetraalkylammonium ions.

Suitable anionic monomers include acrylic acid and methacrylic acid; sulfonic acids such as vinylsulfonic acid and 4-styrenesulfonic acid; (meth)acrylamidophosphonic acids such as (meth)acrylamidoalkylphosphonic acids (e.g., 2-acrylamidoethylphosphonic acid and 3-methacrylamidopropylphosphonic acid); and carboxyalkyl(meth)acrylates such as 2-carboxyethylacrylate, 2-carboxyethylmethacrylate, 3-carboxypropylacrylate, and 3-carboxypropylmethacrylate. Still other suitable acidic monomers include (meth) acryloylamino acids (e.g., N-acryloylglycine, N-acryloylaspartic acid, N-acryloyl-β-alanine, 2-acrylamidoglycolic acid, 3-acrylamido-3-methylbutyric acid, and those described in U.S. Pat. No. 4,157,418 (Heilmann), incorporated herein by reference). Salts of any of these acidic monomers can also be used.

Other suitable anionic monomers may have the general formula (I):

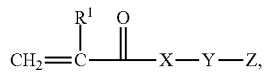

where
R$^1$ is H or CH$_3$;
X is —O— or —NR$^1$—,
Y is a straight or branched chain alkylene, generally from 1 to 10 carbon atoms; and
Z is an anionic group, which may be selected from sulphonic acids groups, phosphonic acid groups, and carboxylic acid groups, and salts thereof.

Some exemplary anionic monomers include (meth)acrylamidosulfonic acids of Formula (II) or salts thereof:

where
R$^1$ is H or CH$_3$, and Y is a straight or branched alkylene having 1 to 10 carbon atoms.

Exemplary ionic monomers according to Formula (II) include, but are not limited to, N-acrylamidomethanesulfonic acid, 2-acrylamidoethanesulfonic acid, 2-acrylamido-2-methylpropanesulfonic acid, and 2-methacrylamido-2-methylpropanesulfonic acid. Salts of these acidic monomers can also be used, examples being (3-sulfopropyl)-methacrylic acid potassium salt and 2-(methacryloyloxy)ethylsulfonic acid sodium salt.

The grafted polymer optionally contains monofunctional ethylenically-unsaturated grafting monomer units having a poly(alkylene oxide) group. These monomers copolymerize with the grafting anionic monomers to form a grafted copolymer chain on the surface of the substrate. When present, these monomers are used in amounts of 2 to 25 wt. %, and more desirably 4 to 20 wt. %, relative to the total monomer weight.

The monomer units having a poly(alkylene oxide) group is of the formula:

Z-Q-(CH(R$^1$)—CH$_2$-Q)$_m$-R$^4$,   III wherein Z is a polymerizable ethylenically unsaturated moiety, R$^1$ is a H or CH$_3$, R$^4$ is a H, a C$_1$ to C$_4$ alkyl group, aryl group, or combinations thereof and m is from 2 to 100, preferably 5 to 20, and Q is a divalent linking group selected from —O—, —NR$^1$—, —CO$_2$— and —CONR$^1$. In one embodiment, the poly(alkylene oxide) group is a poly(ethylene oxide) (co)polymer.

In another embodiment, the pendent poly(alkylene oxide) group is a poly(ethylene oxide-co-propylene oxide) copolymer. Such copolymers may be block copolymers, random copolymers, or gradient copolymers.

Useful ethylenically unsaturated moiety, Z, of the monomer may include:

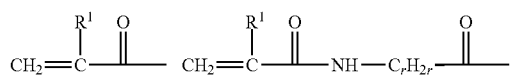

-continued

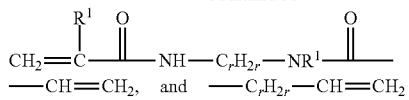

wherein R$^1$ is H or Me and r=1-10.

The monomer having a poly(alkylene oxide) group can be prepared, for example, by reacting mono- or di-functional alkylene oxide (co)polymers (which are typically commercially available) with reactive ethylenically unsaturated compounds (e.g., acrylates). The functional groups terminating the poly(alkylene oxide) may include hydroxy groups, amine groups and carboxyl groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. Preferably, the monomer is prepared by reacting the mono- or di-functional alkylene oxide (co)polymer with (meth)acrylic anhydride. Typically, if a stoichiometric amount of the ethylenically unsaturated reactant is combined with the monofunctional alkylene oxide (co)polymer (such as a monohydroxy terminated alkylene oxide (co)polymer), 100% conversion to the monosubstituted product is obtained.

Examples of suitable monofunctional poly(alkylene oxide) monomers include poly(ethylene oxide) (meth)acrylate, poly(propylene oxide) (meth)acrylate, poly(ethylene oxide-propylene oxide) (meth)acrylate, and combinations thereof. Such monomers preferably include one nonreactive end group such as (C$_1$-C$_4$) alkoxy, aryloxy (e.g., phenoxy), and (C$_1$-C$_4$) alkaryloxy. These groups can be linear or branched. These monomers can be of a wide range of molecular weights and are commercially available from sources such as Sartomer Company, Exton, Pa. (including that methoxy polyethylene obtained under the trade designation "SR550"); Shinnakamura Chemical Co., Ltd., Tokyo, Japan; Aldrich, Milwaukee, Wis.; and Osaka Organic Chemical Ind., Ltd., Osaka, Japan.

Additional examples of suitable neutral hydrophilic monomers include 2-hydroxyethyl(meth)acrylate (HEMA), 2-hydroxypropyl(meth)acrylate, 3-hydroxypropyl(meth) acrylate, 2,3-dihydroxypropyl (meth)acrylate, 4-hydroxybutyl(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, glycerol methacrylate, and combinations thereof. Among these additional examples of suitable neutral hydrophilic monomers, particularly suitable examples include 2-hydroxyethyl(meth)acrylate (HEMA), N-vinyl pyrrolidone, N-vinyl acetamide, methylacrylamide, and mixtures thereof.

In some embodiments neutral hydrophilic monomers can include hydrophilic groups that are any of hydroxyalkyl, methoxyalkyl, polyethyleneglycol, methoxy polyethyleneglycol, or any combination of these.

In some embodiments, the total grafted hydrophilic monomer content may be from 0.75 to 2 times the weight of the plurality of irradiated fibers having grafted pendant hydrophilic groups. The grafted pendant hydrophilic groups extend from the surface of the fibers as a polymer chain. In this grafting method, a repeat unit of the fiber is grafted with a first monomer, which reacts with a second monomer, to grow a polymer chain that extends from the surface of the fiber.

Fibers having grafted pendant hydrophilic groups have an increased ability to absorb water relative to the corresponding non-grafted fibers. In some embodiments, the level of water absorption can increase by more than 10 times. In some embodiments, the level of water absorption can increase by up to 15 times, by up to 20 times, by up to 25 times, or even by up to 30 times.

The water absorbing fibers 14 could be at least 1 mm long or could be less than 300 mm long. In one embodiment, the fibers are at least 10 mm and less than 100 mm long. In one embodiment, the fibers are at least 30 mm and less than 90 mm long. For example, Tencel™ staple fibers (Lenzing, Austria) 1.7 dtex at 51 mm and 3.3 dtext between 60-90 mm are suitable water absorbing fibers. For long input fibers, further fiber chopping could be used to arrive an an appropriate fiber length.

In one embodiment, less than 30% wt. of the adhesive composition comprises the hydrophilic fibers. In one embodiment, less than 10% wt. of the adhesive composition comprises the hydrophilic fibers. In one embodiment, less than 5% of the adhesive composition comprises the hydrophilic fibers. In one embodiment, the fibers comprise between 0.1% to 10% wt. of the adhesive composition.

In one embodiment, the water absorbent fibers 14 may be first blended with one another to form a fibrous article such as a nonwoven web, knitted fabric, woven fabric that is then soaked or coated with the hydrophobic adhesive matrix 12. The adhesive could be either directly delivered (coated) onto the fiber web or transferred from a liner. In one embodiment, the water absorbent fibers 14 are intermixed in the adhesive matrix 12 and then the adhesive composition 10 is coated on to a substrate 25, wherein at least a portion of the water absorbent fibers 14 are exposed at an outer surface of the adhesive composition 10.

In some embodiments, the adhesives composition may include any of a variety of known fillers and additives including, but not limited to, tackifiers (e.g., MQ resins), fillers, pigments, additives for improving adhesion, pharmaceutical agents, cosmetic agents, natural extracts, silicone waxes, and rheology modifiers.

The thickness of the adhesive layer is not particularly limited. In some embodiments, the thickness will be at least 10 microns, and in some embodiments, at least 20 microns. In some embodiments, the thickness will be no greater than 400 microns, and in some embodiments, no greater than 200 microns.

The peel adhesion to biological substrates such as human skin is known to be highly variable. Skin type, location on the body, and other factors can affect results. Generally, average values of peel adhesion from skin are subject to large standard deviations. In some embodiments, the average peel adhesion for human skin may be less than 200 gm/2.54 cm, and in some embodiments, less than 100 gm/2.54 cm.

In some embodiments, the adhesive compositions are suitable for forming medical articles such as tapes, wound dressings, surgical drapes, IV site dressings, a prosthesis, an ostomy or stoma pouch, a buccal patch, or a transdermal patch. In some embodiments, the adhesive compositions may also be useful for other medical articles including dentures and hairpieces.

In some embodiments, the adhesive compositions are suitable for adhering a medical substrate to a biological substrate (e.g., a human or an animal). For example, in some embodiments, the gentle to skin adhesives of the present disclosure may be used to adhere medical substrates to the skin of humans and/or animals. Exemplary medical substrates include polymeric materials, plastics, natural macromolecular materials (e.g., collagen, wood, cork, and leather), paper, films, foams, gels, adhesives, woven cloth and non-woven cloth, metals, glass, ceramics, and composites of one or more of the such materials.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials utilized in the sample preparation are shown in Table 1.

TABLE 1

| Components | | |
|---|---|---|
| Component | Description | Source |
| MQ resin | TMS-803, trimethyl-siloxysilicate | Wacker Chemical Corp., Adrian, MI |
| OHX-4070 | Xiameter ®, hydroxy-terminated dimethyl siloxane, 50,000 cP | Dow Corning, Midland, MI |
| SR550 | Methoxy polyethylene glycol monomethacrylate | Sartomer Company, Exton, PA |
| Tencel ® fiber | Lyocell, regenerated cellulose fiber, 1.3 dtex, 38 mm | Lenzing Fibers, Inc., Lenzing, Austria |
| OasisSAF ® | Acrylic acid, methylacrylate cross-linked polymer fiber | Technical Absorbents, Ltd., Lincolnshire, United Kindom |
| LiquiBlok ™ | HS Fines, sodium polyacrylate particles, 1-140 microns | Emerging Technologies, Inc., Greensboro, NC |
| Tegaderm ™ film | Catalogue number 16002 | 3M Company, St. Paul, MN |
| Tegaderm ™ foam | Catalogue number 90604 | 3M Company, St. Paul, MN |
| Fluorosilicone release liner | Loparex 5100, PET film with fluorosilicone coating | Loparex LLC, Willowbrook, IL |
| Acrylic acid | Acrylic acid | Sigma-Aldrich, St. Louis, MO |

Test Methods
Upright MVTR

The upright MVTR was measured according to ASTM E96-80 using a modified Payne cup method. A 3.8 cm diameter sample was placed between adhesive-containing surfaces of two foil adhesive rings, each having a 5.1 $cm^2$ elliptical opening. The holes of each ring were carefully aligned. Finger pressure was used to form a foil/sample/foil assembly that was flat, wrinkle free, and had no void areas in the exposed sample.

A 120 mL glass jar was filled with approximately 50 g of tap water that contained a couple drops of 0.02% (w/w) aqueous Methylene Blue USP (Basic Blue 9, C.I.52015) solution, unless specifically stated in an example. The jar was fitted with a screw-on cap having a 3.8 cm diameter hole in the center thereof and with a 4.45 cm diameter rubber washer having an approximately 3.6 cm hole in its center The rubber washer was placed on the lip of the jar and foil/sample/foil assembly was placed backing side down on the rubber washer. The lid was then screwed loosely on the jar.

The assembly was placed in a chamber at 40 C and 20% relative humidity for four hours. At the end of four hours, the cap was tightened inside the chamber so that the sample was level with the cap (no bulging) and the rubber washer was in proper seating position.

The foil sample assembly was removed from the chamber and weighed immediately to the nearest 0.01 gram for an initial dry weight, W1. The assembly was then returned to the chamber for at least 18 hours, the exposure time T1 in hours, after which it was removed and weighed immediately to the nearest 0.01 g for a final dry weight, W2. The MVTR in grams of water vapor transmitted per square meter of sample area per 24 hours can then be calculated using the following formula.

$$Upright(Dry)MVTR=(W1-W2)*(4.74*104)/T1$$

Inverted MVTR

The inverted MVTR was measured using the following test procedure. After obtaining the final "dry" weight, W2, as described for the upright MVTR procedures, the assembly was returned to the chamber for at least 18 additional hours of exposure time, T2, with the jars inverted so that the tap water was in direct contact with the test sample. The sample was then removed from the chamber and weighed to the nearest 0.01 gram for a final wet weight, W3. The inverted wet MVTR in grams of water vapor transmitted per square meter of sample area per 24 hours can then be calculated using the following formula.

$$Inverted(Wet)MVTR=(W2-W3)*(4.74*104)/T2$$

Water Absorbency

Water absorbency was the weight difference between a sample which was saturated with water and the same sample which was dried.

Absorption Rate

Absorbing rate test was conducted by laminating adhesive samples on Tegaderm™ foam, adding a drop of colored water to the adhesive surface, and recording the time when water drop disappears.

Grafted Fiber Preparation

Tencel® fibers (6 g) were heat sealed in a plastic bag under a nitrogen atmosphere. The fibers were subjected to electron beam irradiation of 7 MRad. The fibers were added to a monomer solution that had been equilibrated in nitrogen gas environment containing 85 g distilled water, 2-3 g SR550 monomer, 6 g acrylic acid monomer, 21 g sodium chloride and 7 g sodium hydroxide (50%). The fibers were reacted with this monomer solution in a nitrogen atmosphere for 20 hours, follow by a water wash and vacuum filtration. The resulting monomer-grafted fibers were dried at 55 C and processed through a Hergeth random card machine (Aachen, Germany).

Example 1

A mixture was prepared by combining 100 parts OHX-4070, 60 parts TMS-803, 60 parts MQ, and 2% by weight OASIS fiber. This mixture was coated on a fluorosilicone release liner and e-beam cured at 6 MRads and 300 keV. Once cured, the adhesive was transferred to Tegaderm™ film and tested.

Examples 2-11

Additional examples were prepared in a similar manner to Example 1 as described in Table 2.

Comparative

Comparative samples were prepared without absorbing fiber as described in Table 2 using tackifier resin alone or in combination with absorbing particles.

TABLE 2

Adhesive Samples

| | MQ (%) | Absorber | Adhesive Thickness (mil) |
|---|---|---|---|
| Example | | | |
| 1 | 60 | 2% Oasis | 4 |
| 2 | 60 | 2% Oasis | 8 |
| 3 | 60 | 2% Oasis | 12 |
| 4 | 30 | 3% Oasis | 4 |
| 5 | 30 | 3% Oasis | 8 |
| 6 | 30 | 3% Oasis | 12 |
| 7 | 30 | 5% Oasis | 8 |
| 8 | 30 | 7% Oasis | 8 |
| 9 | 30 | 2% grafted fiber | 8 |
| 10 | 60 | 2% grafted fiber | 8 |
| 11 | 60 | 2% grafted fiber | 12 |
| Comparative | | | |
| 1 | 30 | 0 | 4 |
| 2 | 30 | 0 | 8 |
| 3 | 30 | 0 | 12 |
| 4 | 60 | 0 | 4 |
| 5 | 60 | 0 | 8 |
| 6 | 60 | 0 | 12 |
| 7 | 30 | 10% LiquiBlock | 4 |
| 8 | 30 | 10% LiquiBlock | 8 |
| 9 | 30 | 10% LiquiBlock | 12 |
| 10 | 30 | 20% LiquiBlock | 8 |
| 11 | 30 | 30% LiquiBlock | 8 |

TABLE 3

Test Results

| | Upright MVTR (g/m²/ 24 hours) | Inverted MVTR (g/m²/ 24 hours) | Water Absorbance (%) | Absorption Rate |
|---|---|---|---|---|
| Example | | | | |
| 1 | 900 | 6496 | 193 | 5 sec |
| 2 | 821 | 3256 | 89 | 20 sec |
| 3 | 584 | 1588 | 59 | 7 min |
| 4 | 934 | —[a] | 63 | >30 min |
| 5 | 776 | 869 | 63 | >30 min |
| 6 | 514 | — | 31 | >30 min |
| 7 | 737 | 1106 | 125 | 1 min |
| 8 | 763 | 1255 | 148 | 1 min |
| 9 | 829 | 1659 | 28 | <5 sec |
| 10 | — | 2966 | — | — |
| 11 | — | 2853 | — | — |
| Comparative | | | | |
| 1 | 829 | 922 | 10 | >30 min |
| 2 | 579 | 492 | 10 | >30 min |
| 3 | 368 | 412 | 9 | >30 min |
| 4 | 797 | 904 | — | >30 min |
| 5 | 474 | 544 | — | >30 min |
| 6 | 371 | 430 | — | >30 min |
| 7 | 829 | 1044 | 63 | >30 min |
| 8 | 526 | 588 | 30 | >30 min |
| 9 | 355 | 430 | 22 | >30 min |
| 10 | 685 | 829 | 54 | >30 min |
| 11 | 882 | 1114 | 74 | >30 min |

[a]not measured

What is claimed is:

1. An adhesive composition comprising:
   a radiation crosslinked hydrophobic adhesive; and
   a plurality of water absorbent fibers dispersed throughout the hydrophobic adhesive, wherein at least a portion of the fibers are exposed at an outer surface of the adhesive composition and at least a portion of the fibers contact one another at mutual points of contact, wherein between 0.1% and 10% wt. of the adhesive composition is the absorbent fibers.

2. The adhesive composition of claim 1, wherein the hydrophobic adhesive is a hydrophobic silicone.

3. The adhesive composition of claim 2, wherein the silicone comprises a crosslinked poly diorganosiloxane.

4. The adhesive composition of claim 3, wherein poly diorganosiloxane material comprises a poly dimethylsiloxane.

5. The adhesive composition of claim 4, wherein the poly dimethylsiloxane is selected from the group consisting of one or more silanol terminated poly dimethylsiloxanes, one or more non-functional poly dimethylsiloxanes, and combinations thereof.

6. The adhesive composition of claim 5, wherein the poly dimethylsiloxane consists of one or more non-functional poly dimethylsiloxanes.

7. The adhesive composition of claim 1, wherein the adhesive further comprises a silicate resin tackifier.

8. The adhesive composition of claim 1, wherein the adhesive further comprises a poly(dimethylsiloxane-oxamide) linear copolymer.

9. The adhesive composition of claim 1, wherein the absorbent fiber comprises a natural hydrophilic fiber, synthetic hydrophilic fiber, semisynthetic hydrophilic fiber, grafted hydrophilic fiber, a superabsorbent fiber or combinations thereof.

10. A medical article comprising:
a medical substrate;
a layer of an adhesive comprising a radiation crosslinked hydrophobic adhesive; and
a plurality of water absorbent fibers dispersed throughout the hydrophobic adhesive, wherein at least a portion of the fibers are exposed at an outer surface of the adhesive composition and at least a portion of the fibers contact one another at mutual points of contact,
wherein between 0.1% and 10% wt. of the adhesive composition is the absorbent fibers.

11. The article of claim 10, wherein the layer has a thickness of 20 to 200 microns.

12. The article according claim 10, wherein the medical substrate comprises at least one of paper, polymeric film, foam, woven fabric, foil, adhesive, gel, and non-woven fabric, or combinations of one or more thereof.

13. The article according to claim 10, wherein at least a portion of the water absorbent fibers contact the substrate.

14. The adhesive composition of claim 10, wherein the hydrophobic adhesive is selected from the group consisting of a hydrophobic silicone, non polar acrylic, hydrophobic urethane, polyolefin, natural rubber, synthetic rubber, or combination of one or more thereof.

* * * * *

UNITED STATES PATENT AND TRADEMARK OFFICE
CERTIFICATE OF CORRECTION

PATENT NO.       : 9,919,073 B2
APPLICATION NO.  : 14/237367
DATED            : March 20, 2018
INVENTOR(S)      : Junkang Liu Page 1 of 1

It is certified that error appears in the above-identified patent and that said Letters Patent is hereby corrected as shown below:

In the Specification

Column 5
Line 17    Delete "one is" and insert -- one in --, therefor.
Line 25    Delete "alky" and insert -- alkyl --, therefor.
Line 51    Delete "W" and insert -- R' --, therefor.

Column 7
Line 66    Delete "polyoxyethelenes," and insert -- polyoxyethylenes, --, therefor.
Line 66    Delete "polyoxpropylenes," and insert -- polyoxypropylenes, --, therefor.

Column 11
Line 13    Delete "dtext" and insert -- dtex --, therefor.
Line 15    After "arrive" delete "an" and insert -- at --, therefor.

Column 12
Line 34 (Including Table 1)    Delete "Kindom" and insert -- Kingdom --, therefor.
Line 66    Delete "40 C" and insert -- 40° C. --, therefor.

Column 13
Line 45    Delete "55 C" and insert -- 55° C. --, therefor.

In the Claims

Column 16
Line 16    Claim 12, after "according" insert -- to --.

Signed and Sealed this
Fifteenth Day of May, 2018

Andrei Iancu
*Director of the United States Patent and Trademark Office*